United States Patent [19]

Horvitz et al.

[11] 4,069,232

[45] Jan. 17, 1978

[54] MANUFACTURE OF GAMMA-BUTYROLACTONES FROM 1,3-GLYCOLS AND ESTERS, HALIDES AND METADIOXANES THEREOF

[75] Inventors: David Horvitz; William D. Baugh, both of Cincinnati, Ohio

[73] Assignee: National Distillers and Chemical Corporation, New York, N.Y.

[21] Appl. No.: 641,800

[22] Filed: Dec. 18, 1975

[51] Int. Cl.² ............................................ C07D 307/20
[52] U.S. Cl. .................................................. 260/343.6
[58] Field of Search ................... 260/343.6, 496, 340.7

[56] References Cited

U.S. PATENT DOCUMENTS

| 3,458,532 | 7/1969 | Hayden | 260/343.6 |
|---|---|---|---|
| 3,509,209 | 4/1970 | Fenton | 260/533 |
| 3,586,698 | 6/1971 | Ishii et al. | 260/340.7 |
| 3,813,428 | 5/1974 | Paulik et al. | 260/532 |
| 3,952,020 | 4/1976 | Stapp | 260/343.6 |

FOREIGN PATENT DOCUMENTS 1,941,448   3/1970   Germany.

OTHER PUBLICATIONS

Roberts, *Friedel—Crafts & Related Reactions*, Olah, Ed., vol. II, pp. 1175–1210.
Arundale, et al., *Chem. Rev.* 51: 505–555 (1952).
Reppe et al., *Ann.* 582: 72–116 (1953).
Walker, *Formaldehyde*, 3rd Ed., Reinhold Pub. Corp., N. Y., 1964, pp. 416–428.

*Primary Examiner*—Richard L. Raymond
*Attorney, Agent, or Firm*—Kenneth D. Tremain

[57] ABSTRACT

Gamma-butyrolactones are manufactured from olefins by reacting an olefin with an aldehyde to produce a 1,3-difunctional compound, reacting the 1,3-difunctional compound with carbon monoxide, and thereafter recovering the lactone thus produced.

9 Claims, No Drawings

MANUFACTURE OF GAMMA-BUTYROLACTONES FROM 1,3-GLYCOLS AND ESTERS, HALIDES AND METADIOXANES THEREOF

BACKGROUND OF THE INVENTION

Gamma-butyrolactones are used in the chemical industry as solvents and also as chemical intermediates. The lactones can be converted to 1,4-diols, to tetrahydrofurans, and to pyrrolidone derivatives. For example, gamma-butyrolactone can be converted into 1,4-butanediol, tetrahydrofuran or pyrrolidone, all of which are important industrial chemicals.

Gamma-butyrolactones are manufactured presently by two principal methods. The first involves the sequence of reacting acetylene with formaldehyde to produce 1,4-butynediol, hydrogenating the 1,4-butynediol to 1,4-butanediol, followed by dehydrogenation to gamma-butyrolactone. The second primary method involves the hydrogenation of maleic anhydride or succinic anhydride.

German patent 1,066,572 teaches that trimethylene oxide can be carbonylated to produce gamma-butyrolactone in the presence of metal carbonyls as catalyst. Heck, J.Amer.Chem.Soc. 85, 1460 (1963) teaches that trimethylene oxide can be reacted with carbon monoxide and cobalt hydrocarbonyl to form 4-hydroxybutyrylcobalt tetracarbonyl, which, in turn, reacts with dicyclohexylethylamine to produce cobalt carbonyl anion and gamma-butyrolactone.

A new method of producing gamma-butyrolactones has been discovered which involves reacting olefins with aldehydes to obtain a 1,3-difunctional compound which is thereafter reacted with carbon monoxide to form the lactone which is subsequently recovered. The method of the present invention is advantageous in that lower cost starting materials can be employed and a much wider variety of gamma-butyrolactone derivatives can be produced.

Accordingly, it is the object of this invention to provide a new method for the manufacture of butyrolactones from olefins. This and other objects of the invention will become apparent to those skilled in the art from the following detailed description.

SUMMARY OF THE INVENTION

This invention relates to a process for the production of gamma-butyrolactones and more particularly relates to a process wherein olefins and aldehydes are reacted to produce 1,3-difunctional compounds which are then further reacted with carbon monoxide under suitable reaction conditions, and the lactones thus produced are recovered.

DESCRIPTION OF THE PREFERRED EMBODIMENTS

In the first step of the instant process, an olefin and an aldehyde are reacted so as to form a 1,3-difunctional compound. The olefins which can be used in this step include any of the mono- or diolefins containing 2-18 carbon atoms. The olefins can be substituted with aromatic, alicyclic or heterocyclic groups and the unsaturation can exist at any part of the olefinic carbon atom chain and also in cyclic moieties. Both conjugated and nonconjugated diolefins can be employed. Thus, among the olefins which can be used in this invention are ethylene, propylene, butene-1, cis- and transbutene-2, isobutylene, hexene-2, diisobutylene, trimethylethylene, 1,5-hexadiene, cyclohexane, cyclopentadiene, butadiene, isoprene, 1,4-pentadiene, 1,3-hexadiene, cyclooctadiene, 1-sec-butyl-2-methylethylene, 7-n-propyl-octene-3, styrene, alpha-methylstyrene, propenylbenzene, beta-vinylnaphthalene, beta-vinylpyridine, and the like.

The aldehydes employed in the first reaction step contain 1-18 carbon atoms, one or two aldehyde groups and can also contain aromatic, alicyclic or heterocyclic groups. Additionally, the aldehyde reactant can also be in any form which readily generates the aldehyde such as in the form of an acetal or semi-acetal, a bisulfite addition product, a bis-methylene ester, or a cyclic or linear oligomer. Examples of aldehydes or aldehyde-generating compounds which can be employed include formaldehyde, paraformaldehyde, trioxane, methylal, hexamethylene tetramine, formaldoxime, sodium formaldehydesulfoxylate, acetaldehyde, propionaldehyde, n-butyraldehyde, benzaldehyde, cyclopentane carboxaldehyde, terephthaldehyde, beta-pyridinecarboxaldehyde, alpha-naphthaldehyde, and the like.

The reaction of the olefins and aldehydes to produce 1,3-difunctional compounds is known and does not, per se, form a part of this invention. Many modifications of the reaction are also described in the literature. For example, see Arundale & Mikeska, Chem. Revs. 51, 505–55 (1952); Roberts, *FriedelCraft and Related Reactions*, Olah ed., Volume II, pages 1175–1210, Inter Science Publishers, New York, 1964; Walker, *Formaldehyde*, 3rd Ed. Reinhold Publishing Corp., New York, 1964, pages 416–28; and U.S. Pat. No. 3,586,698.

The olefin-aldehyde reaction can take place under conditions of acid catalysis (both protic acids and Lewis acids), noble metal salt catalysis, and even thermally without added catalyst. The method and conditions employed depend greatly on the particular olefin and aldehyde used and the type of product desired.

The reaction of olefins with aldehydes in the presence of protic acids as catalysts is described in the aforesaid Mikeska & Arundale article.

The production of 1,3-difunctional compounds by the reaction of olefins with aldehydes in the presence of protic acids as catalysts is preferred in producing the lactones of the instant invention. The preferred protic acids are hydriodic acid and hydrobromic acid because these two acids serve as promoters during the subsequent reaction with carbon monoxide. It has been found advantageous to use these acids in a concentration which corresponds to 0.1 N to 7.5 N and preferably 0.3 N to 2 N.

In the protic acid catalyzed reaction, it is possible to obtain the metadioxanes, glycols, or esters depending on the conditions which are used. Acid concentration, temperature and duration of the reaction vary with the product desired and the nature of the olefin. In the presence of organic acids, such as formic, acetic, benzoic and similar acids, the corresponding esters are obtained. The concentration of aldehyde can vary from 0.1 M to 15 M with a preferred range of 0.2 M to 5 M. The solvent can be water or a carboxylic acid, such as formic acid, acetic acid, propionic acid, etc., or a combination of water and an organic acid. The olefin can serve as a solvent, or other organic solvents, and reaction inert liquids can be used, e.g., aliphatic or aromatic hydrocarbons such as hexane, cyclohexane, benzene, chlorobenzene or dichloroethane. The olefin should be present in a mole ratio relative to the aldehyde of at least 0.5:1 but can be present in any excess greater than that ratio. In general, a ratio of olefin to aldehyde of 1:1 to 2:1 is preferred. However, when a gaseous or highly volatile olefin is used, such as ethylene or propylene, elevated pressures are desirable to obtain sufficient solubility, and in such cases, the ratio of olefins to aldehydes may be in considerable excess over the 2:1 ratio. The temperature to be used in the reaction depends greatly on the olefin employed and can vary from ambient temperature to 250° C. The preferred temperature in the case of ethylene is 120°-200° C. The preferred duration of reaction is also strongly dependent on the olefin and aldehyde used and on the acid concentration. The time required can vary from 15 minutes to 10 hours.

The products of the reaction between the olefins and aldehydes are 1,3-difunctional compounds of the formula

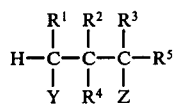

in which $R^1$, $R^2$, $R^3$, $R^4$ and $R^5$ are from the group consisting of hydrogen, alkyl aryl, cycloalkyl, aralkyl, alkaryl or heterocyclic groups of 1–18 carbon atoms, Y and Z are each hydroxyl, $R^6COO-$, Cl, Br, I or E, or together are $-OCH(R^1)O-$, E is an oxygen-bonded inorganic ester moiety such as nitrate, sulfate, phosphate, borate, arsenate and the like, and $R^6$ is hydrogen, alkyl of 1–18 carbon atoms, aryl of 6–18 carbon atoms, alkaryl of 6–18 carbon atoms or aralkyl of 6–18 carbon atoms. $R^2$ and $R^3$ together may comprise a trimethylene or tetramethylene group to form a 5- or 6-membered alicyclic structure with the two carbon atoms on which they are substituted. The group $R^1$ is the group which is part of the aldehyde, $R^1CHO$, which is reacted with an olefin to produce the described 1,3-difunctional compound. When diolefins are employed, corresponding 1,3-difunctional groups may be produced at each double bond.

Examples of 1,3-difunctional compounds produced in the first step of the instant invention include 1,3-dioxane, 1,3-diacetoxypropane, 3-hydroxypropyl acetate, 3-hydroxypropyl iodide, 3-iodopropyl acetate, 1,3-diiodopropane, 1,3-propanediol, 4,4-dimethyl-1,3-dioxane, 5,5-dimethyl-1,3-dioxane, 3-hydroxypropyl bromide, 3-bromopropyl acetate, 1,3-dibromopropane, and the like.

When the 1,3-difunctional compounds are reacted with carbon monoxide in accordance with the present invention, gamma-butyrolactone derivatives of the formula

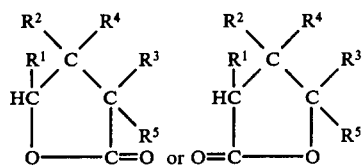

or a mixture of the two compounds is produced. When the carbon atoms of the 1,3-difunctional compounds shown above are symmetrically substituted, exclusive of Y and Z, only a single gamma-butyrolactone derivative is found. For example, 1,3-propanediol, 3-iodopropanol, 3-hydroxypropyl acetate and 1,3-dioxane all give the same product (gamma-butyrolactone) with carbon monoxide in accordance with this invention.

When a diolefin has been reacted with an aldehyde, in the first step, to produce a compound with two 1,3-difunctional groupings, subsequent carbonylation can produce mixtures of compounds containing two butyrolactone rings in the same molecule.

Economic advantages can be achieved if the reaction mixture from the aldehyde-olefin reaction can be subjected to the reaction with carbon monoxide without intermediate separation, isolation or purification procedures. As noted above, it is advantageous, when using acid catalysis, to employ hydriodic or hydrobromic acid as the catalyst because iodides and bromides serve as promoters in the carbon monoxide reaction. However, it is also possible to have such promoters present when other acids or catalysts are used, or it is possible to add such promoters to the 1,3-difunctional compounds which have been produced and/or isolated. When the 1,3-difunctional compounds are produced thermally without catalysts or by Lewis acid or noble metal salt catalysis, the promoters can be present initially or added just prior to the carbon monoxide reaction.

Although the 1,3-difunctional compounds include 1,3-dioxane and its derivatives, it has been found advantageous to minimize the production of such compounds and to maximize the production of the other designated types of 1,3-difunctional compounds. In the case of the dioxanes, an equivalent amount of aldehyde enters into formation of the compound which does not subsequently enter into the formation of the butyrolactones and must therefore either be recycled or lost. The 1,3-dioxane and its derivatives can be minimized or eliminated in accordance with known procedures. When using hydrobromic or hydriodic acids as catalysts, however, it has been found that the formation of the dioxanes can be minimized by using less water, more organic acid, more hydrogen halide and higher temperatures. Further, it is found that in the presence of transition metal salts, to be subsequently employed in the carbon monoxide reaction, the formation of 1,3-dioxanes is virtually eliminated when hydriodic or hydrobromic catalysis is used in the presence of organic acids.

It is known in the art that an organic hydroxylic compound can be reacted with carbon monoxide in the presence of a suitable catalyst to form a carboxylic acid containing one or more carbon atoms than it possessed initially, the carbon monoxide moiety, in fact, being inserted between the carbon atom and the oxygen atom of the hydroxyl group attached to it. For example, acetic acid can be produced from methanol by reaction with carbon monoxide. Copenhaver & Bigelow, *Acetylene and Carbon Monoxide Chemistry* (Reinhold Publishing Co., New York 1949) state at page 274

"As catalysts for the reaction, phosphoric acid, phosphates, activated carbon, heavy metal salts such as zinc and cuprous chlorides, oxides and silicates of chromium, molybdenum, tungsten, uranium, oxides of thorium, zirconium, titanium, aluminum and magnesium and boron fluoride have been suggested."

Compounds containing two hydroxyl groups can produce dicarboxylic acids containing two more carbon atoms than the initial compound. However, the kind of product obtained appears to vary with the number of carbon atoms which separate the hydroxyl groups from each other, the catalyst employed and the operating conditions.

It is also known that halides, esters and ether derivatives can react with carbon monoxide in a similar fashion. For example, Reppe et al. describe in Ann. 582, 72-116 (1953), carbonylation of tetrahydrofuran to adipic acid and δ-valerolactone (pages 87-89) and butylbromide to valeric acid (page 106). Paulik et al, in German Offen. No. 1,941,448, state that non-vicinal halides, esters and ether derivatives, in addition to glycols, can be carbonylated to dicarboxylic acids.

In accordance with the present invention, the reaction products of the initial aldehyde-olefin reaction are reacted with carbon monoxide in the presence of a suitable catalyst to produce the corresponding butyrolactone derivatives. As earlier indicated, the products of the first step can be 1,3-glycols, their esters, their halides or meta-dioxanes. When a mixture of such substances is present, they all react in the subsequent carbonylation reaction to produce the butyrolactones.

It has not previously been reported that the 1,3-difunctional compounds can be carbonylated to gamma-butyrolactones and on the contrary, only production of dicarboxylic acids has been reported (see Examples 2 and 8 in the German Offen., Reppe at pages 75 and 85, and Example 12 in U.S. Pat. No. 3,813,428). In the German Offen., it is reported that 1,5-dicarboxylic acid is a major product and that no significant amount of by-products are formed. The U.S. patent makes reference to a small amount of monocarboxylic acid formation (about 1 mole percent), presumably a butyric acid, from 1,3-propanediol. Reppe reports formation of a mixture of adipic acid and methylglutaric acid from 1,3-butanediol. It has now been found that gamma-butyrolactones can be made the major product of the reaction with essentially complete exclusion of dicarboxylic acid formation and with almost complete conversion of the 1,3-difunctional precursors, by maintaining suitable control of the conditions of reaction. The control which must be maintained is that of the entire carbonylation system and it is believed that the butyrolactone formation is the result of the reactivity of the 1,3-difunctional precursors being so much greater than the reactivity of the butyrolactones.

The chief consideration in the control of reactivity is time, but the latter is in turn dependent on the other parameters of the reaction which affect the rate of reaction. That is, if the reaction is halted soon enough, essentially only butyrolactones will be found present. Factors affecting the rate of carbonylation for any particular 1,3-difunctional compound or compounds are: temperature, pressure, the nature and amounts of promoter and of catalyst, the amount of water present and the solvent. The specific time limitation therefore, has to be determined for each system. The important finding of this invention is that regardless of the variables, it is possible to find a range of times in which the γ-butyrolactones can be produced as the major products, with essentially no formation of dicarboxylic acids, the difference in reaction rates allowing a fairly wide latitude of conditions.

In general, the catalysts most useful for the carbonylation are the metals and the compounds and complexes of the metals of Group VIII of the Periodic Table. Iron, cobalt and nickel can be used in the form of the powdered or finely divided metals, as compounds from which the carbonyls are formed under the carbonylation conditions, as the iodides, acetates, formates, carbonates, etc., or as the carbonyls, as $Ni(CO)_4$, $Fe(CO)_5$, or $Co_2(CO)_8$, for example. Promoters used with these catalysts are bromides or iodides, preferably the latter. The iodide can be furnished as the iodide of the metal catalyst or as hydrogen iodide, iodine, or as a metal iodide, the metal being from Groups I, II, III, IV, V or VIA of the Periodic Table. The amount of time required for production of the gamma-butyrolactone with minimal formation of dicarboxylic acid must be determined for the particular precursor that is used and for the catalyst and reaction parameters.

The noble metals of Group VIII can also be used as carbonylation catalysts in the form of the finely divided metals or as their salts, oxides or complexes. They also require a bromide or iodide promoter, which can be added in the forms mentioned previously for iron, nickel and cobalt, but may also be added as an organic bromide or iodide, especially as aliphatic halides. The time of reaction is controlled for maximization of the gamma-butyrolactones and to avoid formation of any dicarboxylic acids. The Group VIII metal catalysts can comprise about 0.01-10% by weight of the reaction mixture with a preferred amount of about 0.05-2%. The promoter halogen should be present in an amount ranging from about 1.0-40% by weight of the reaction mixture with a preferred range of about 2-20%.

The reaction temperature is generally about 120°-325° C. and the CO partial pressure is generally about 1-500 atmospheres or more. When noble metal catalysts are employed, it is preferred to employ a CO partial pressure of 1-200 atmospheres and a temperature of about 120°-250° C. When other Group VIII catalysts are used, a CO partial pressure of 50-500 atmospheres and a temperature of 160°-325° C. are preferred.

The carbonylation reactions can be conducted with the 1,3-difunctional precursors in the absence of any solvent or it can be conducted in the presence of water, carboxylic acids, such as acetic or propionic acids, hydrocarbon solvents such as benzene, toluene, cyclohexane, heptane, xylene, chlorinated aromatics, such as chlorobenzene, o-dichlorobenzene, etc. and mixtures thereof.

An illustrative procedure for the production of gamma-butyrolactone from ethylene, formaldehyde and carbon monoxide is as follows:

Step 1. Ethylene, at 1000 psi, is introduced into a pressure vessel containing 9% formaldehyde, 25% water, 53% acetic acid, and 13% hydrogen iodide. The vessel is heated with agitation to 145° C. for 6 hours, while ethylene is added as required to maintain its partial pressure. The vessel is cooled and the ethylene released.

Step 2. To the solution of Step 1 is added 0.2 weight percent rhodium chloride. The solution is now pressurized with carbon monoxide to 1000 psi and the vessel is heated with agitation at 175° C. for 6 hours. Carbon monoxide is added as required during the reaction. The vessel is cooled and the carbon monoxide is released.

Step 3. An equal weight of water is added to the products and the resulting solution is extracted with benzene to remove the gamma-butyrolactone. The benzene extract is distilled to obtain the gamma-butyrolactone in pure form.

The description given is only illustrative and this procedure can take many forms depending on the reactants and conditions employed. It is possible, for example, to allow the hot solution from Step 1 to leave the pressure vessel, without relieving the ethylene pressure or cooling the solution, and after release of dissolved ethylene pumping the solution into another pressure vessel, which is under carbon monoxide pressure, catalyst being added simultaneously, and thereby conducting Step 2 with minimum loss of heat or gas pressure. The product from Step 2 can be released also without relieving the carbon monoxide pressure. Thus, the steps of the reaction can be run in continuous fashion. The catalyst can be recycled to Step 2 from the aqueous solution, after the butyrolactone has been extracted, the solution having been appropriately concentrated by distillation. It is also possible to introduce the recycled catalyst at Step 1. Similarly, the other reactants can be recycled after suitable separation and concentration. Higher olefins can be reacted with aldehydes in a Step 1 that does not require pressure. When Step 1 is conducted with a catalyst which is not a promoter for Step 2, the promoter (and its recycle) can be added either at Step 1 or Step 2.

The following Examples are set forth to further illustrate the present invention without being limited thereby. Throughout this specification and claims, all parts and percentages are by weight and all temperatures in degrees Centigrade unless otherwise specified.

EXAMPLE 1

A solution containing 2.5 mls formalin, 14.5 mls acetic acid and 3 mls of 57% hydriodic acid was placed in a glass liner of a stainless steel pressure vessel. Ethylene gas was introduced at a pressure of 850 psi, and the reactor was heated to 145° C. for 8 hours, agitation being provided by shaking. An examination by gas liquid chromatography, (GLC) of the contents of the reaction product showed the presence of major amounts of 1,3-dioxane and 1,3-diacetoxypropane, and lesser amounts of 3-hydroxypropylacetate, 3-hydroxypropyliodide, 3-iodopropylacetate, and 1,3-diiodopropane. To the reaction mixture was added 0.05 g of $RhCl_3.XH_2O$ (42.29% Rh). The mixture was put back in the reactor, pressured with 1500 psi of carbon monoxide and heated to 175° C. for 10 hours with shaking. The final product contained 9.5 millimoles of gamma-butyrolactone (28.5% yield on formaldehyde initially introduced) and a small amount of 1,3-diiodopropane. No glutaric acid was detected.

EXAMPLE 2

A solution containing 2.5 mls formalin, 9.5 mls acetic acid, 5 mls water and 3 mls of 57% hydriodic acid was reacted as in Example 1 by pressurizing with 850 psi of ethylene and heating at 145° C. for 8 hours. Examination of the product showed major amounts of 1,3-dioxane and 1,3-diacetoxypropane, with lesser amounts of 3-hydroxypropylacetate, 3-hydroxypropyliodide, and 3-iodopropylacetate. To this mixture was added 0.05 g $RhCl_3.XH_2O$. It was then pressurized with 1500 psi of carbon monoxide and heated with shaking at 175° C. for 10 hours. Examination of the products showed the presence of 7.1 millimoles of gamma-butyrolactone (21.3% yield on formaldehyde initially introduced) and no glutaric acid. Appreciable quantities of 1,3-diacetoxypropane and 3-iodopropylacetate were still present.

EXAMPLE 3

Example 1 was repeated using an initial reaction solution containing 2.5 ml formalin, 13.5 ml acetic acid and 4 mls of 57% hydriodic acid. After the reaction with ethylene, a similar spectrum of products was present. 0.05 g $RhCl_3.XH_2O$ was added and the reaction with carbon monoxide was also conducted as in Example 1. The final product contained 8.9 millimoles of gamma-butyrolactone (26.8% conversion on the formaldehyde) and some 1,3-diiodopropane. No glutaric acid was observed.

EXAMPLE 4

A solution containing 2.5 mls formalin, 14.5 mls acetic acid, 3 mls of 57% hydriodic acid and 0.05 g $RhCl_3.XH_2O$ was pressurized with ethylene to 900 psi and heated with shaking at 145° C. for 8 hours. Examination of the products showed 1,3-diacetoxypropane, 3-iodopropylacetate and 3-hydroxypropyliodide to be present in major amounts. No significant quantity of other precursors was present. The unaltered reaction mixture was placed under 1500 psi of carbon monoxide and heated with shaking at 175° C. for 8 hours. The product contained 7.0 millimoles of gamma-butyrolactone (20.9% conversion on the formaldehyde) and a small amount of diiodopropane. No other precursors were left, and no glutaric acid was observed.

EXAMPLE 5

A reaction was conducted as in Example 4, except that the starting solution contained 0.5 g of an alumina-supported rhodium metal (5% rhodium) instead of $RhCl_3.XH_2O$. The product, after the ethylene reaction, contained the same precursors as found in Example 4, with insignificant amounts of any other precursors. After the reaction with carbon monoxide, there were found 5.6 millimoles of gamma-butyrolactone (16.9% conversion based on the formaldehyde). No glutaric acid was found and appreciable amounts of the precursors were still present.

EXAMPLE 6

A solution containing 2 g paraformaldehyde, 9 mls water, 8 mls acetic acid and 3 mls of 57% hydriodic acid was placed in the reactor and pressurized with 875 psi of ethylene. The mixture was heated with shaking at 145° C. for 8 hours. The product was found to contain the precursors: 1,3-dioxane, 1,3-propanediol, 3-hydroxypropylacetate, 3-hydroxypropyliodide, 1,3-diacetoxypropane, 3-iodopropylacetate and 1,3-diiodopropane. To this solution was added 0.1 g $RhCl_3.XH_2O$ and it was pressurized with carbon monoxide to 2000 psi and heated with shaking at 175° C. for 7 hours. The final product was found to contain 10.9 millimoles of gamma-butyrolactone (16.3% conversion on the initially used paraformaldehyde). No glutaric acid was produced, and insignificant amounts of the precursors were present.

EXAMPLE 7

A solution containing 2 g paraformaldehyde, 5 mls water, 12 mls acetic acid and 3 mls of 57% hydriodic acid was placed under a pressure of 140 psi of propylene gas and then heated with shaking at 130° C. for 6 hours. The products were found to contain mixtures of 1,3-difunctional precursors including two isomeric methyl-1,3-dioxanes and hydroxy, iodo, and acetoxy-substituted compounds. To this mixture was added 0.1 g $RhCl_3.XH_2O$ and the solution was placed under 1500 psi of carbon monoxide. It was heated with shaking to 175° C. for 6 hours. About 22.2 millimoles of methyl-gamma-butyrolactones were formed (33.2% conversion on the paraformaldehyde initially introduced). No dicarboxylic acids were detected.

EXAMPLE 8

5.6 g isobutylene were added to a solution of 44 g 1,4-dioxane, 6.4 g concentrated sulfuric acid and 6.0 g trioxane in a glass pressure tube equipped with stirrer and pressure gauge. The mixture was stirred at ambient temperature about 16 hours. The volatiles were evaporated under vacuum and the residue washed with water and then extracted with benzene. The benzene was removed. The product contained about 95% 4,4-dimethyl-1,3-dioxane and about 5%, 5,5-dimethyl-1,3-dioxane. 4 mls of this product was added to a solution of 7 mls water, 7 mls acetic acid, 3 mls of 57% hydriodic acid and 0.1 g $RhCl_3.XH_2O$. This solution was placed in a pressure vessel and pressurized with 1500 psi of carbon monoxide and heated with shaking at 175° C. for 6 hours. The dimethyl-1,3-dioxanes were converted essentially quantitatively to the dimethyl-gamma-butyrolactones (determined by GLC and confirmed by mass spectroscopy). No dicarboxylic acids were formed.

EXAMPLE 9

The following reactions were conducted to show how time and conditions determine whether a dicarboxylic acid is found.

Reaction A involved placing a solution of 1 ml 1,3-propanediol, 16 mls acetic acid, 3 mls of 57% hydriodic acid and 0.0125 g $RhCl_3.XH_2O$ under 1000 psi of carbon monoxide and heated with shaking at 200° C. for 5 hours. The product was found to contain 7.35 millimoles of gamma-butyrolactone (53.1% yield) and no glutaric acid.

The reaction mixture was returned to the autoclave under 1000 psi carbon monoxide and heated and shaken at 200° C. for 10 more hours. The product now contained 10.95 millimoles of gamma-butyrolactone (79.2% yield) and again no glutaric acid could be detected.

Reaction B was the same as Reaction A, but contained more catalyst, i.e., 0.05 g $RhCl_3.XH_2O$. It was treated the same way as Reaction A. At the end of the first 5 hours, the product contained 9.67 millimoles of gamma-butyrolactone (69.8% yield) and no glutaric acid could be detected. At the end of 10 more hours of treatment the product was found to contain 10.82 millimoles of gamma-butyrolactone (78.3% yield) and about 1.5 millimoles of glutaric acid.

EXAMPLE 10

A solution containing 2 mls 1,3-propanediol, 15 mls water, 3 mls of 57% hydriodic acid and 0.1 g $RhCl_3.XH_2O$ were placed in an autoclave, pressurized with 1200 psi of carbon monoxide, and heated with shaking at 175° C. for 6 hours. Analysis indicated the presence of 7.8 millimoles of gamma-butyrolactones (28.2% conversion based on the propanediol introduced). Unreacted propanediol and 3-hydroxypropyliodide were also present. The solution was returned to the autoclave, pressurized with 1100 psi of carbon monoxide and heated at 175° C. for 6 hours more. The product now contained 15.1 millimoles of gamma-butyrolactone (54.4% conversion), but some 3-hydroxypropyliodide was also present. No glutaric acid was formed.

EXAMPLE 11

A solution containing 2 mls 1,3-propanediol, 10 mls water and 5 mls acetic acid, 3 mls of 57% hydriodic acid and 0.1 g $RhCl_3.XH_2O$ was placed in an autoclave under 1200 psi of carbon monoxide and heated with shaking at 175° C. for 6 hours. The product was found to contain 15.2 millimoles of gamma-butyrolactone (54.7% conversion). There were also present 3-hydroxypropylacetate, 3-hydroxypropyliodide, 3-iodopropylacetate and 1,3-diiodopropane. The mixture was returned to the autoclave, pressurized with 1100 psi carbon monoxide and heated with shaking at 175° C. for 6 hours more. The product was found to contain 20.4 millimoles of gamma-butyrolactone (73.6% conversion) and no significant amount of precursors. No glutaric acid was observed.

EXAMPLE 12

A solution of 2 mls 1,3-propanediol, 12 mls acetic acid and 4 mls water was refluxed for 2 hours. An analysis (by GLC) of the resulting solution indicated the presence of 4.1 millimoles 1,3-propanediol, 8.9 millimoles 3-hydroxypropylacetate and 14.7 millimoles of 1,3-diacetoxypropane. To this solution were added 2 mls of 57% hydriodic acid and 0.1 g $RhCl_3.XH_2O$. The solution was placed in an autoclave under 1000 psi of carbon monoxide, and it was heated with shaking at 175° C. for 6 hours. The product was found to contain 17.2 millimoles of gamma-butyrolactone (62.0% conversion, based on precursors) and some 1,3-diacetoxypropane, 3-iodopropylacetate and a very small amount of 1,3-diiodopropane. No glutaric acid was observed.

EXAMPLE 13

A solution of 1 ml 1,3-propanediol, 13 mls water and 6 mls of 57% hydriodic acid was refluxed for 2 hours. The solution was then found to contain 12.85 millimoles of 3-hydroxypropyliodide and a small amount of residual 1,3-propanediol. To this solution was added 0.1 g $RhCl_3.XH_2O$. It was placed in an autoclave under 1000 psi of carbon monoxide and heated with shaking at 175° C. for 6 hours. The produce was found to contain 13.2 millimoles of gamma-butyrolactone (95.5% conversion based on precursors) and no residual precursors. No glutaric acid was observed.

EXAMPLE 14

A mixture containing 1 ml 1,3-diiodopropane, 19 mls water and 0.1 g $RhCl_3.XH_2O$ was placed in an autoclave under 1070 psi of carbon monoxide and heated with shaking at 175° C. for 6 hours. The product was found to contain 1.54 millimoles of gamma-butyrolactone (18.2% conversion based on the diiodopropane) and 2.3 millimoles of 3-hydroxypropyliodide. No glutaric acid was observed.

EXAMPLE 15

A solution containing 3 mls 1,3-dioxane, 14 mls water, 3 mls of 57% hydriodic acid and 0.1 g $RhCl_3.XH_2O$ was placed in an autoclave under 2350 psi of carbon monoxide and heated with shaking at 200° C. for 5 hours. The product was found to contain 21.8 millimoles of gamma-butyrolactone (61.7% conversion). No glutaric acid was observed.

EXAMPLE 16

A solution containing 2 mls gamma-butyrolactone, 10 mls water, 5 mls acetic acid, 3 mls of 57% hydriodic acid and 0.05 g $RhCl_3.XH_2O$ was placed in an autoclave under 1500 psi carbon monoxide and heated with shaking at 175° C. for 6 hours. The product was found to contain 3.0 millimoles of glutaric acid (11.4% conversion), most of the gamma-butyrolactone being unreacted.

EXAMPLE 17

A solution containing 1 ml 1,3-propanediol, 7 mls acetic acid, 6 mls water and 6 mls of 41% hydrobromic acid was refluxed for 2 hours. The resulting solution was found to contain a mixture of 3-hydroxypropylbromide, 3-hydroxypropylacetate and 3-bromopropylacetate. The solution was placed in an autoclave under 1000 psi of carbon monoxide and heated with shaking at 175° C. for 7 hours. The product contained 2.3 millimoles of gamma-butyrolactone (16.8% conversion based on the precursors) together with some residual 3-hydroxypropylbromide and 1,3-dibromopropane. No glutaric acid was found.

EXAMPLE 18

A solution containing 2.5 mls formalin, 14.5 mls acetic acid, 3 mls of 57% hydriodic acid and 0.5 g of activated carbon containing 5% palladium was placed in an autoclave under 890 psi of ethylene and heated with shaking at 145° C. for 8.5 hours. The product was found to contain 1,3-diacetoxypropane as a major product with lesser amounts of 1,3-dioxane, 3-hydroxypropylacetate, 3-hydroxypropyliodide, and 3-iodopropylacetate. This solution was put back into the autoclave under 1500 psi of carbon monoxide and heated with shaking at 175° C. for 8 hours. The resulting mixture was found to contain 2.0 millimoles of gamma-butyrolactone (6.0% conversion based on formaldehyde initially used). Some residual diacetoxypropane and iodopropylacetate were also present. No glutaric acid was observed.

EXAMPLE 19

A solution containing 2 mls 1,3-propanediol, 15 mls water, 3 mls of 57% hydriodic acid, 0.2 ml pyridine and 0.2 g $PdCl_2$ was placed in an autoclave under 2350 psi of carbon monoxide and heated with shaking at 200° C. for 5 hours. The product was found to contain 1.44 millimoles of gamma-butyrolactone (5.2% conversion based on the propanediol), and no glutaric acid.

EXAMPLE 20

A solution containing 1 g paraformaldehyde, 17 mls acetic acid, and 3 mls of 57% hydriodic acid was placed under 950 psi of ethylene and heated with shaking at 160° C. for 8 hours. The product was found to contain no significant amount of 1,3-dioxane, although other precursors were present, the major ones being 1,3-diacetoxypropane and 3-iodopropylacetate. To the solution was added 0.05 g $RhCl_3.XH_2O$, and it was pressurized to 1500 psi with carbon monoxide and heated with shaking at 175° C. for 8 hours. The product was found to contain 9.2 millimoles of gamma-butyrolactone (27.7% conversion based on the paraformaldehyde). No glutaric acid was observed.

EXAMPLE 21

A solution containing 1 g paraformaldehyde, 18 mls acetic acid and 2 mls of 57% hydriodic acid was placed under 950 psi of ethylene and heated with shaking at 160° C. for 8 hours. The product contained no 1,3-dioxane, but did contain other precursors, the main ones being 1,3-diacetoxypropane and 3-iodopropylacetate. There were also present 3-iodopropanol and 3-hydroxypropylacetate in much smaller amounts. To this solution was added 0.1 g of a hydrate of $IrCl_3$. The solution was pressurized with 1500 psi of carbon monoxide and heated with shaking at 175° C. for 8 hours. The product of the reaction was found to contain 2.05 millimoles of gamma-butyrolactone (6.2% conversion based on the paraformaldehyde). No glutaric acid was detected.

EXAMPLE 22

A solution containing 1 ml 1,3-propanediol, 9 mls water, 9 mls acetic acid, 2 mls of 57% hydriodic acid and 0.1 g $CoI_2$ was placed under 1500 psi carbon monoxide and heated with shaking at 200° C. for 10 hours. Examination of the reaction product showed the presence of 1.07 millimoles of gamma-butyrolactone (7.7% conversion based on the propanediol). No glutaric acid was observed.

EXAMPLE 23

A solution containing 1 ml 1,3-propanediol, 9 mls water, 9 mls acetic acid, 2 mls of 57% hydriodic acid and 0.1 g $NiCO_3$ was placed under 1500 psi of carbon monoxide and heated with shaking at 200° C. for 10 hours. The product contained 0.53 millimoles of gamma-butyrolactone (3.9% conversion based on the propanediol). No glutaric acid was observed.

EXAMPLE 24

A solution containing 1 ml 1,3-propanediol, 9 mls water, 9 mls acetic acid, 2 mls of 57% hydriodic acid and 0.1 g $Fe_2O_3$ was placed under 1500 psi of carbon monoxide and heated with shaking at 200° C. for 10 hours. The product was found to contain 1.34 millimoles of gamma-butyrolactone (9.7% conversion based on the propanediol). No glutaric acid was observed.

EXAMPLE 25

A solution containing 1 g paraformaldehyde, 19 mls o-dichlorobenzene and 0.5 g $ZnCl_2$ was placed under 900 psi of ethylene and heated with shaking at 150° C. for 8 hours. The resulting mixture was found to contain 1,3-dioxane, and after adding 1 ml of n-propyliodide as promoter and 0.05 g of $RhCl_3.XH_2O$ as catalyst, it was placed under 1500 psi of carbon monoxide and heated with shaking at 175° C. for 8 hours. Analysis of the product showed the presence of 0.66 millimoles of gamma-butyrolactone (2.0% conversion), and no glutaric acid.

Various changes and modifications can be made in the process of this invention without departing from the spirit and the scope thereof. The various embodiments set forth herein were illustrative only and were not intended to limit the invention.

We claim:

1. A method of manufacturing gamma-butyrolactones which comprises reacting
 a 1,3 difunctional compound selected from the group consisting of 1,3 glycols, the esters, halides and metadioxanes thereof, and mixtures thereof
 with carbon monoxide at a partial pressure of 1 to 500 atmospheres and at a temperature of 120° to 325° C.
 in the presence of a catalytic amount of from about 0.01 to 10 weight percent, based upon the reaction mixture, of a Group VIII element in the form of the metal or a compound or complex thereof
 and in the presence of from about 1.0 to 40 weight percent of an iodine or bromine promoter for said catalyst said reacting being conducted for a period of between about 5 and 15 hours, sufficient to produce gamma-butyrolactone as a major product, and isolating and recovering said gamma-butyrolactone.

2. The method of claim 1, wherein said reacting is conducted in the presence of a solvent selected from the group consisting of water, carboxylic acid, hydrocarbon, chlorinated aromatic hydrocarbon and mixtures thereof.

3. The method of claim 1 wherein said 1,3 difunctional compound is selected from the group consisting of 1,3 dioxane, 1,3-diacetoxypropane, 3-hydroxypropyl acetate, 3-hydroxypropyl iodide, 3-iodopropyl acetate, 1,3-diiodopropane, 1,3-propanediol, 4,4-dimethyl-1,3-dioxane, 5,5-dimethyl-1,3-dioxane, 3-hydroxypropyl bromide, 3-bromopropyl acetate, 1,3-dibromo propane and mixtures thereof.

4. The method of claim 1 wherein the catalyst is about 0.05-2% and the halogen promoter is about 2-20% of the reaction mixture.

5. The method of claim 1 wherein the Group VIII metal is iron, cobalt or nickel, and an iodine promoter is used.

6. The method of claim 5 wherein the iodine is present in the form of the anion of the metal catalyst, hydrogen iodide, iodine or a metal iodide where the metal is selected from Groups I, II, III, IV, V or VIA of the Periodic Table.

7. The method of claim 1, wherein said Group VIII element is a noble metal.

8. The method of claim 7 wherein an iodine promoter is employed and the iodine is in the form of the anion of the metal catalyst, hydrogen iodide, iodine or a metal iodide where the metal is selected from Groups I, II, III, IV, V or VIA of the Periodic Table or an organic iodide.

9. The method of claim 8 wherein the Group VIII element is Rh.

* * * * *